United States Patent [19]

Nordlund

[11] 4,166,483
[45] Sep. 4, 1979

[54] PROGRAMMABLE FRACTION COLLECTOR

[75] Inventor: Lage A. Nordlund, Uppsala, Sweden

[73] Assignee: Pharmacia Fine Chemicals, Sweden

[21] Appl. No.: 856,386

[22] Filed: Dec. 1, 1977

[30] Foreign Application Priority Data

Dec. 14, 1976 [SE] Sweden .............................. 7614077

[51] Int. Cl.² .............................................. B65B 3/04
[52] U.S. Cl. ....................................... 141/1; 141/284;
422/67; 364/107
[58] Field of Search ............................... 141/250–284,
141/1–12; 23/253 R, 259; 364/107; 422/63, 67

[56] References Cited
U.S. PATENT DOCUMENTS 3,625,265  12/1971  Gilson ................................ 141/284

Primary Examiner—Houston S. Bell
Attorney, Agent, or Firm—Seidel, Gonda, Goldhammer & Panitch

[57] ABSTRACT

A device for filling test containers with drops of fluid under test with the containers arranged in rows and columns while permitting automatic movement of the drop discharge device to preselected coordinate positions. The center to center distance between adjacent containers may vary from row to row. Stopping drop discharge device at a particular coordinate position (hence a particular container) until a preselected volume of fluid has been dispensed by the drop discharge or until a preselected time interval has expired.

16 Claims, 5 Drawing Figures

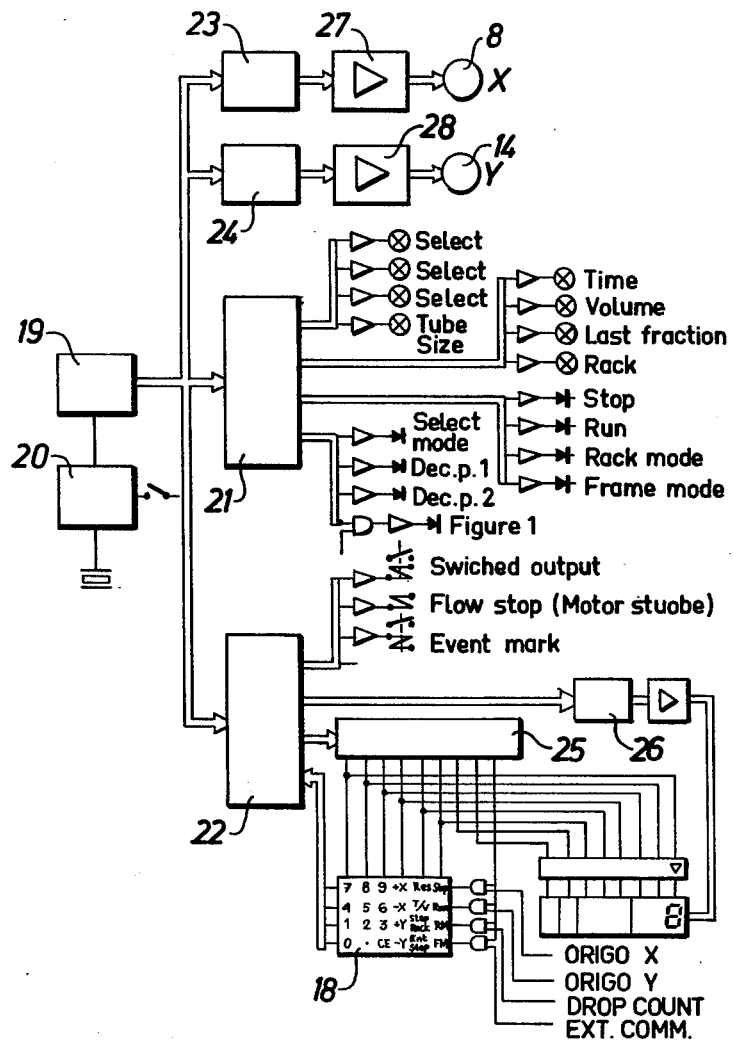

PROGRAMMABLE FRACTION COLLECTOR

The present invention relates generally to an apparatus for giving off samples to test containers. Specifically the invention relates to a programmable fraction collector in which fractions of a fluid under test are collected in separate test containers. In a known fraction collector the test containers, generally test glasses, are arranged in rows and columns. A carriage with a drop discharge device, e.g. a filler tube, for the fluid under test is movable backwards and forwards along the test glass rows and columns, respectively. In this known fraction collector fractions of a predetermined volume of the fluid are collected in each test glass. In this connection the carriage moves forwards and backwards over successive test glass columns in a meander-like pattern. This known fraction collector has the disadvantage that a large number of test glasses are required to fraction a fluid that has been obtained for instance by column filtering. Each test glass is, one after the other, filled with a certain amount of fluid and after the fractionation the test glasses containing the fluid of interest are analysed, while the contents of the remaining test glasses is thown away. A typical fractionation process lasts for instance about 12 hours and the number of filled test glasses can be of the order of 200. Of these 200 test glasses usually only about 5 glasses are interesting, which means that the contents of the remaining 195 test glasses have to be thrown away and that these 195 test glasses have to be dished and cleaned without more or less due course.

Instead of filling the test glasses on volume basis it is alternatively possible to fill the test glasses on time basis, i.e. that a carriage with a filler tube stops over each test glass during a predetermined interval of time.

Disadvantages with this known fraction collector are apparent. Despite the fact that one in advance knows approximately when the fractions that are interesting for the analyzis will occure in connection with column filtering and despite the fact that one knows after approximately what volume these interesting fractions will occur, one is forced to fill a very large number of test glasses so to speak without due course.

Swedish Pat. specification No. 7207504-7 discloses a fraction collector, in which the arrangement of the test glasses is not tied to a once and for all determined pattern of test glasses, but can be easily varied for different such patterns. Further it is also possible to change the order in which the glasses are to be filled. Information concerning the desired disposition pattern and the desired fill order is present in form of marks on a so-called program plate. To each desired disposition and fill order pattern there corresponds a so-called program plate. A large library of program plates is thus required to make it possible to use the fraction collector at least in connection with a few main types of test glass disposition patterns. The necessity for such a program library is of course a disadvantage.

In order to control the discharge device for the test glasses, which thus can be arranged differently in different fractionations, a feed back control system is used, which senses the marks on the program card corresponding to the locations of the test glasses. Each mark contains information regarding the identity of and the direction to the next test glass to be filled. The control system comprises photo-electric cells that are fixed on a movable arm of the disclosed type, on which a carriage with a drop discharge device is movable. The control system senses said information and starts driving motors for the arm and carriage movement when a new glass is to be filled. During the transportation of the arm the photocells sense the program card and transmit stop signals to the motors when a mark is reached, which corresponds to the test glass to be filled.

One disadvantage with the program plates according to this known Swedish specification is that the plates are exposed to wearing when they are put in and taken out of the fraction collector, which can lead to damaging of marks and thus to that the carriage with the drop discharge device will not be controlled correctly in accordance with the intended fill pattern.

One object of the present invention is to provide a fraction collector that enables movement of the drop discharge device according to any desired pattern over test glasses disposed on a base plate. It shall be possible to use test glasses of different sizes in one and the same fractionation process, it being possible to collect for instance fractions that are not of interest in large test glasses, while interesting fractions can be collected in small test glasses. Furthermore it shall be possible to fill a test glass with the drop discharge device either on volume basis or on time basis, and it shall be possible to change without limitations between filling on volume basis and time basis, respectively, during a fractionation process. Furthermore it shall be possible to select the time and the number of drops for filling a test glass within wide limits. Thus, it shall be possible to adapt the size of the test glasses and their location to each fractionation process that can occur.

The characterising features of the invention are disclosed in the attached patent claims.

The number of point patterns that can be stored in the program memory is a finite number, that is very large and that is determined mostly by only the dimensions of the base plate in relation to the centre-to-centre distance for the test glasses used and the length of the shortest transportation step of the stepping motors.

According to the invention test glasses that are all of the same size are divided into groups. One group consists of a certain number of glasses, that are arranged in for instance one or several test glass holders. In each holder there can be one or several rows of test glasses. The holders are positioned in rows in side-by-side relationship to each other on a base plate. The test glasses in one and the same group are accordingly of the same size while, as mentioned above, sizes of test glasses in different groups can be chosen to be different.

The order in which test glasses in a group are filled is determined in advance in the shown embodiment of the invention and is determined by the number of test glass rows in the test glass holder of the group. The first row in a test glass holder is always filled from for instance left to right. If a holder only has one row of test glasses the carriage after filling this row returns to the left before the first row in the next holder is filled. If a holder has two rows of test glasses a first row is filled from the left to the right and the second row from the right to the left, whereafter the carriage is in a new starting position for filling the first test glass row of the next holder from the left. According to the invention it is possible to determine in advance the number of test glasses in a row that are to be filled. Accordingly not all the glasses in a row have to be filled before the carriage continues to the following test glass row.

The advantages with the apparatus according to the invention are apparent. By using test glasses of large size for fractions that are not of interest and test glasses of smaller size for fractions of interest the number of required test glasses for performing a complete fractionation is reduced. Furthermore, since it is possible to select the volume which (or the time interval during which) one wishes to fill the test glasses in a group and by setting the number of test glasses in this group that one wants to fill, it is possible to optimize the total number of test glasses that are necessary for the fractionation. Thus, eluate that is not of interest in the subsequent analyzis is preferably collected in a few large test glasses instead of a large number of small test glasses, as previously done. On the other hand it is possible to use small test glasses and fill them with very small quantities, some times maybe only a few drops, of fractions of the eluate that is of interest in the subsequent analyzis.

The selection of test glass size, of the filling of test glasses in a group either on time basis or volume basis, and the selection of the order in which the test glasses are to be filled is represented by parameters used in subroutines of a fixed program for controlling a carriage, which program has been determined in advance. These parameters are stored in a program memory with a suitable input means, which can comprise for instance a paper tape reader, a magnet card or any other type of information carrier, but which in a prefered embodiment of the invention comprises a key set with function keys and numerical keys. A display unit indicates for the operator the order in which the function keys and the numerical keys shall be handled, which means that also a person that has no programming experience easily can handle the fraction collector in accordance with the invention. Thus, the staff of the laboratory does not need to have special knowledge in programming to be able to handle the fraction collector in accordance with the present invention. The program according to which the parameters that have been inputted through the input means shall be used is fixed and stored in a ROM-memory (read only memory), while the parameters inputted by the operator are temporarily stored in RAM-memories (random access memory). The flow of data between the memories is controlled by a central micro processor (CPU) in accordance with a fixed control program.

When the operator has specified the parameters he pushes a key marked "RUN" and the whole fractionation process is then automatically performed, a process that can last from a few hours up to about 20 hours or more.

The invention will be further described below, where reference is made to the attached drawings, on which FIG. 1 shows a top view of a fraction collector in accordance with the present invention;

FIG. 5 shows a block diagram of all of the electrical equipment that is contained in the fraction collector.

Figure 1:
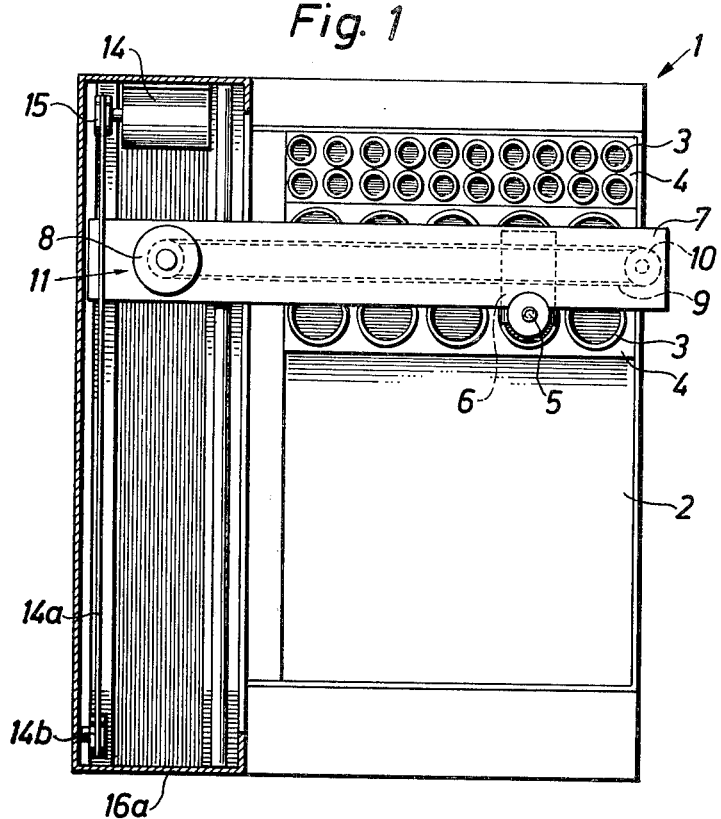

FIG. 1 shows a fraction collector 1 in accordance with a preferred embodiment of the present invention. On a base plate 2 a number of test glasses 3 are arranged in separate test glass holders 4. The test glasses 3 can be of different size, as is shown in the Figure. In the embodiment described below it is assumed that three different test glass sizes are present, which are designated 1, 2 and 3, respectively. Size 1 is the smallest (a diameter of the order of 8-12 mm), size 2 is somewhat bigger (a diameter of the order of 12-18 mm), while size 3 is the largest test glass size (a diameter of the order of 18-38 mm). Each holder can contain a certain number of test glasses. In the embodiment shown a holder for test glasses of size 3 can take five test glasses in a row. A holder for test glasses of size 2 can take twenty test glasses arranged in two rows that are arranged side-by-side as is indicated by the Figure. A test glass holder for test glasses of size 1 is in the known embodiment assumed to be able to take thirty test glasses arranged in two rows of fifteen glasses each. However, the invention is not restricted to the number of sizes, of glasses per holder or the arrangement of the glasses in each holder mentioned above. The test glasses 3 are filled in rows, on after the other, with a fraction of an eluate to be analysed later. The eluate can for instance be obtained by column filtering. The eluate is filled into the test glasses with a discharge device 5, for instance a filler tube arranged on a carriage 6 that is movable in two perpendicular directions. The carriage 6 is movably journalled on an arm 7, which also carries a stepping motor 8, which by means of wires 9 or the like and a pulley 10 transports the carriage 6 in one direction or the other along a test glass row. The aggregate formed by the units 7-10 forms a first driving mechanism 11 for the carriage 6. This first driving mechanism is supported on a carriage 12 (FIG. 2) that runs on railes 13. The carriage supports the arm 7 and is driven by a second stepping motor 14 by means of a wire 14a that is fixed in the carriage and that runs over a pulley 14b. The rotation of the motor 14 is thus transfered into translational movement for the carriage 12, and thus also for the first driving mechanism 11, in a direction that is perpendicular to the direction of movement of the carriage 6. The units 12-14 form a second driving mechanism 15 for the carriage 12.

Figure 2:
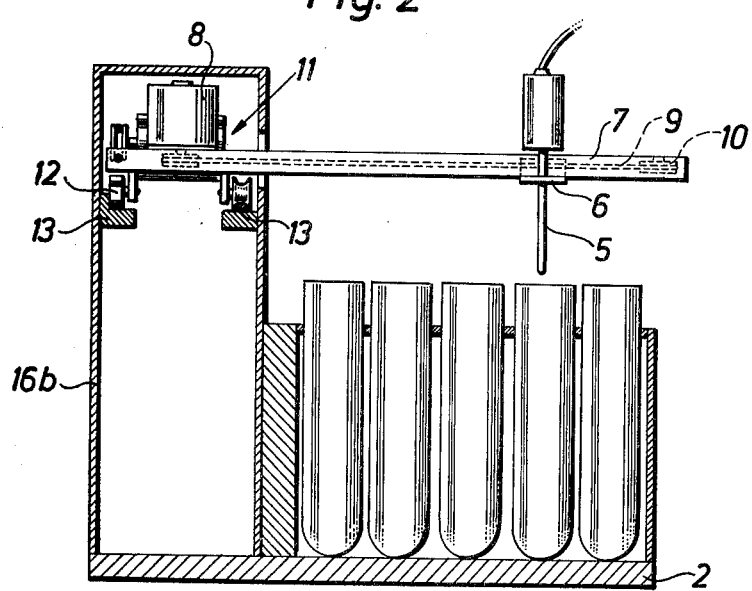
FIG. 2 shows a front view of the fraction collector of FIG. 1.
Figure 3:
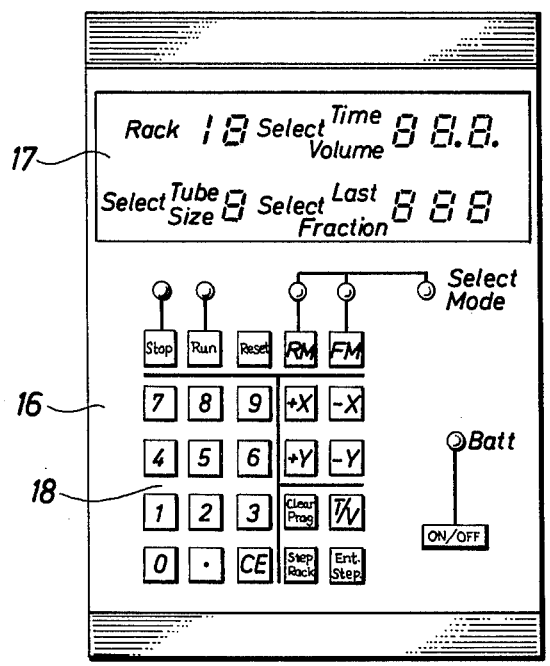
FIG. 3 shows a detailed view of the control panel of the fraction collector.

In FIG. 2 there is shown an elevational view of the fraction collector of FIG. 1. From a control panel 16 that is shown in FIG. 3 an operator can program the fraction collector in order to make it perform a series of tasks, which are individual and adopted by the operator to the fractionation that is to be performed. The control panel 16 comprises a presentation display 17 and a key set 18 with function keys and numerical keys. The control panel can be arranged in the front wall 16a of the house 16b, that encloses the driving mechanisms 11 and 15.

FIG. 3 shows the control unit 16 in detail. The presentation display has text fields, in which the individual letters and figures are shining with for instance red colour. The individual figures are of seven-segment type. The key set 18 comprises keys for figures 0-9 and for decimal point. Furthermore there are provided a number of function keys STOP, RUN, RESET, RM, FM, +X, −X, +Y, −Y, CLEAR-PROG, T/V, STEP-RACK, ENTER STEP. Furthermore there is provided an ON/OFF-switch. The round rings above the function keys STOP, RUN, RM, FM represent light emitting diodes, which shine when the corresponding key has been pushed. Above the ON/OFF-key there is provided a light emitting diode marked "BATTERY", which is shining when there is a mains failure to indicate that the fraction collector is driven by a spare battery than enables operation for one more hour. The battery is automatically switched in when a mains failure occurs.

Figure 4:
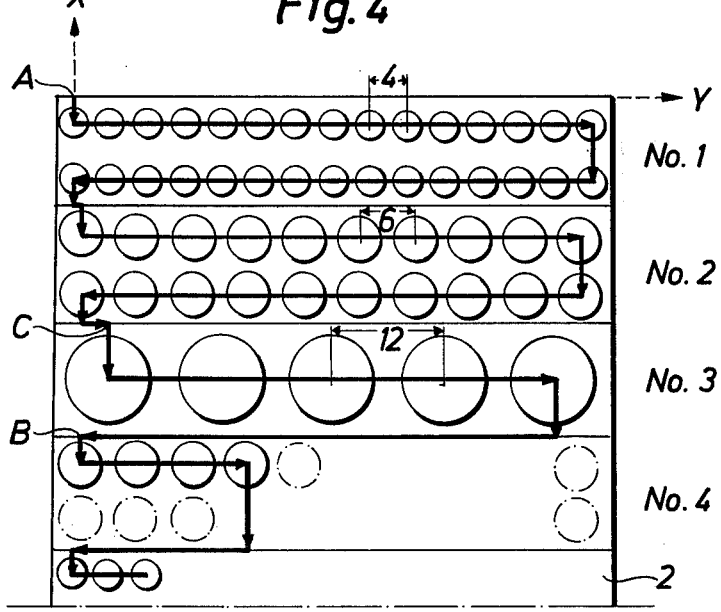
FIG. 4 shows an example of a movement pattern for the discharge means and use of test glasses of different size in one and the same fractionation process.

FIG. 4 shows a number of basic disposition patterns for test glasses of different size and a number of basic movement patterns for discharge device in connection with filling test glasses of sizes 1, 2 and 3. The holders are assumed to be arranged on the base plate 2. Each holder is indicated with a rectangel. A base plate is assumed to be divided into a right-angled coordinate system X-Y in which one unit of length is a base length in a module system, one module in the example shown being equal to 3.8 mm. The total span of the base plate is X=56 modules (=212.8 mm) and Y=117 modules (=444.6 mm). The centre-to-centre distance between test glasses of size 1 is 4 modules (=15.2 mm), between test glasses of size 2 it is 6 modules (=22.8 mm) and for test glasses of size 3 it is 12 modules (=45.6 mm). The base plate takes ten test glass holders. The stepping motors have an adjustment accuracy of ±1 mm and move with a mean velocity of 20 mm/s in successive and much shorter steps. In FIG. 4 the centre-to-centre distances and certain other distances have been indicated with figures, which are expressed in modules.

As regards the patterns for the arrangement of the test glasses the following applies: The test glass holders are so constructed and arranged on the base plate as to make the centre-to-centre distances for each test glass always to coincide with some point that can be formed in said right-angled coordinate system by two integer multiples (along the X-axis and Y-axis respectively) of the base length (=module length). Accordingly a point pattern that corresponds to the centre points for the test glasses arranged on the base plate is formed. When the plate is filled with test glasses of only size 1a rather compact point pattern that corresponds to the placing of the test glasses on the base plate is formed. When the plate is filled with test glasses of only size 2 a thinner point pattern is formed and when it is filled with test glasses of size 3 a very thin point pattern is formed. The number of test glasses in the present test glass arrangement on the plate influences of course the appearance of point patterns. To each of these three basic point patterns, which thus have many variants, that are determined by the number of used or selected glasses, there corresponds an origin or a starting point for the drop discharge device and a movement scheme for the discharge device. In the case where a test glass holder has two rows of glasses (as is the case for glass or tube sizes 1 and 2) the movement scheme is meander-like as is indicated at points 1, 2 and 4 in FIG. 4. If a holder only has one test glass row the movement scheme is from the left to the right accompanied by a return to a point directly over the centre point of the first glass in the next holder. However, it must be stressed that each movement scheme in principle can be chosen arbitrarily and that the schemes or patterns shown are not intended to restrict the invention. For instance the patterns can be chosen in such a way that only every second glass in a row is filled during the fractionation process. The remaining glasses can then for instance be filled in a separate analysing process, for instance by suction of the content in a filled glass and by transferring that amount of fluid to the adjacent, empty glass.

Each of the three main types of point patterns mentioned above can then be assumed to be divided into sub-patterns that correspond to centre points for test glasses in only one test glass holder. Thereby three new main types of point patterns of varying density are obtained, for instance points A, B and C in FIG. 4. It is then possible in an arbitrary way to combine the sub-point patterns mentioned above with each other, each combination corresponding to the arrangement of the test glass holders arranged on the base plate, which holders accordingly on the one hand can be filled with test glasses, the size of which varies from holer to holder and on the other hand can be only partly filled, that is each test glass in a holder does not necessarily have to be filled.

It is now possible by suitable programming to store each of all these possible combinations of arrangement patterns of test glasses in a memory together with all the movement schemes that corresponds to each arrangement combination.

FIG. 5 shows a block diagram of the motor control and programming unit in the fraction collector according to the invention. A central micro processor (CPU) 19 is controlled by a clock pulse generator 20 in order to in suitable time order collect instructions from ROM-memories 21 and 22, in which the control program for the whole fraction collector and every possible point and movement pattern is stored. Data that have been fed in from the feed in unit in the form of a key set 18 are stored in RAM-memories 23, 24. The key set 18 is cyclically scanned with a BCD-decoder 25 for determining whether a key is pushed in or not. The control program for the micro dator has a facility that makes it possible for the CPU 19 to tell the difference between unintentional key pushings, so-called key bounces, and intentional pushings. The BCD-decoder also controls the presentation units 17 synchronously with the scanning of the key set. A decoder 26 convertes BCD-coded figures to a so-called 7-segment code. The stepping motors 8 and 14, respectively, are driven by corresponding buffer amplifiers 27 and 28, respectively, which on orders from the CPU generate strobe or activation pulses to the corresponding stepping motor. Each activation pulse that is sent to the corresponding stepping motor is counted and the accumulated number of activation pulses, which thus represents the position of the drop discharge device in the X- and Y-direction, respectively, is continuously compared in the corresponding RAM-memory 23 and 24 respectively with the points of the point pattern that has been chosen by the input device 18 (which points are now collected from a table in the memory 21). When coincidence occurs in one of the directions X or Y the motors are stopped. Which one of the stepping motors that is then to be activated is determined by the actual movement scheme called for. The mentioned test between the points in the chosen point pattern and the accumulated number of activation pulses is thus performed by means of separate test routines, that are stored in one of the ROM-memories 21, 22. Alternatively the test can be made by means of separate comparators (that are not shown) (one for the X-direction and one for the Y-direction), one input of each comparator receiving a number from the memory 21 corresponding to the corresponding coordinate (in X- and Y-direction, respectively) for the points of the chosen point pattern, and the other input receiving the accumulated number of activation pulses that continuously are stored in a corresponding counter for each of the directions X and Y, respectively. Accordingly the control system for the stepping motors is of the open type. Whether the drop discharge device actually reaches the centre point of the corresponding test glass is not sensed or checked by the control unit.

Finally there are a number of outputs from the memories 21 and 22 in FIG. 5. Adjacent to the top of memory 21 there are four outputs, namely SELECT (3) and TUBE SIZE, followed by another group of four outputs, namely TIME, VOLUME, LAST FRACTION and RACK. These eight outputs represent lamps or text fields, that shine on the control panel in connection with the loading of a program, as will be explained in detail below. Furthermore there is a group of four outputs, which are designated the names STOP, RUN, RACK MODE and FRAME MODE and which are all connected to lamps, that according to FIG. 3 are located above the corresponding function key. Finally there is a group of four outputs designated SELECT MODE, DEC.PKT 1, DEC.PKT 2 and SIFFRAN 1, of which the first is connected to the lamp at the function key SELECT MODE shown in FIG. 3, the two following are connected to the two decimal points in the presentation unit, and the last is connected to the presentation unit in order to show the FIG. 1 at the display RACK when the function key RM is pushed. Finally from the memory 22 there is a group of three outputs, which are connected to one relay each. The first output, designated SWITCHED OUTPUT (200 V) is activated when the last test glass in the last holder has been filled, whereafter the line current is interrupted and the fraction collector is switched off. The second output (FLOW STOP, MOTOR STROBE) activates its relay just before each occation when an activation pulse is sent to one of the stepping motors. When the relay is activated it closes the drop discharge device so as to prevent it from dropping while it is transorted between the test glasses. The third output EVENT MARK is also activated just before movement of one of the stepping motors and this output can be used for registration of the movements of the discharge device on for instance a printer. Finally there are four AND-gate-controlled inputs to the input unit 18. These inputs are called ORIGIN X, ORIGIN Y, DROP COUNT and EXTERNAL COMMAND. All of the second inputs of the AND-gates are jointly connected to an output of BCK-decoder 25. The input origin X is connected to a read yoke (not shown) that senses if the drop discharge device 5 is in the point X=0. Similarly another read yoke (not shown) senses if the drop discharge device is in the point Y=0. The input drop count is connected to a drop sensor (not shown), that emits a signal each time the drop discharge device discharges a drop. In the event of a signal on the input EXTERNAL COMMAND the whole automatic control system is set aside and the fraction collector can be controlled manually.

In connection with the loading of a program from the key set the operator first has to choose if the apparatus shall work in so-called FRAME MODE och so-called RACK MODE, which he does by pushing the key FM och RM.

Selection of the function FM (frame mode) presupposes that the test glasses on the base plate are of one and the same size. The operator shall then choose how many of these test glasses that shall be filled either with an optional volume, that is same for all the chosen test glasses, or during an optional period of time, that is equal for all the chosen test glasses. Accordingly the function FM corresponds to the mode of operation of a conventional fraction collector.

selection of the function RM (rack mode; rack=test glass holder) presupposes that test glass holders (filled with empty test glasses) are arranged in rows (the size of the test glasses can be different from holder to holder) on the base plate in an order (as concerns the size of the test glasses) that corresponds to the present fractionation. By means of the key set 18 the operator then feeds into a certain memory in the fraction collector information concerning the filling of the test glasses in each test glass holder. The glasses in a holder are in this case considered as a common group and the programming is performed for each holder and starts from the first test glass holder (holder No. 1) on the base plate. The holders are continuously numbered and in the preferred embodiment a maximum of ten holders can be arranged on the base plate. The information fed in for each test glass holder concerns:

(1) the size of the test glasses in the present holder (abbreviated to TS; tube size);

(2) whether the filling of the glasses in the present holder shall be performed on time basis or volume basis (abbreviated below to T and V, respectively; time and volume, respectively);

(3) the number of minutes (optional between 0.1 minute to a maximum of 999 minutes) during which the discharge device shall drop in each of a selected number of test glasses in the present holder, or if the filling shall be performed on volume basis, the number of drops (optional between 1 and a maximum of 999 drops) that is to be dropped in the selected number of glasses in the present holder;

(4) the number of glasses in the group that are to be filled (optional between 1 and a maximum of the largest number of glasses for the present test glass holder). This number is designated "last fraction".

Thus, it is possible to vary these four parameters from holder to holder.

Selection of the function ENTER STEP means that the numerical keys that have been pushed in the key set (figures concerning for instance tube size, fill volume or fill time and number of selected tubes in a group) is fed into the special memory. This feeding is done along the principles of so-called polish notation. If the key ENTER STEP is pushed twice in succession just before the selection according to point 4 this means that the preceding parameter (according to points 1, 2 or 3 above) shall apply for all test glasses in the present holder. Accordingly if ENTER STEP has been pushed twice in succession selection according to point 4 is not necessary.

Selection of the function RUN means that the program fed in is automatically performed.

Selection of the function CLEAR PROGRAM means that a program that has been previously fed in by means of the key set is deleted.

Selection of the function STOP means that the automatic execution of the program can be interrupted and that the operator can control the movement of the discharge device on the key board by pushing the function keys +X, −X, +Y, −Y. Selection of the key +X means that the discharge device steps forward to the test glass that is located in the adjacent X-position. In this connection one thinks of the base plate as being divided into a coordinate pattern with perpendicular and Y-axis. The X- and Y-axis are divided into a number of unit length, where one unit length forms the base length in a module system, in which the centre points for the test glasses (of sizes 1, 2 and 3) in the test glass holders can be specified in the coordinate system. In the same way a push on the function key —X will mean that the discharge device will step backwards to the test glass that has the adjacent, programmed +-position. Similar functions apply for the function keys +Y and —Y, which concern corresponding movements in the Y-direction.

With the key CE an incorrectly fed in figure combination is corrected.

With the key T/V there is a transition from measurement of time to measurement of drops.

With the key STEP RACK the parameters fed in by the operator are checked holder by holder. When the operator pushes this key the selected parameters for the previous holder are presented on the display 17.

When the key "RESET" is pushed the discharge device returns to its initial position.

In order to show how the fraction collector can be programmed in the different modes two examples will be described below.

EXAMPLE 1

FRAME MODE. One wishes to fill 65 test glasses of size 2 during 3.5 minutes each. Four test glass holders with twenty test glasses each (of size 2) are arranged in a row on the base plate.

The operator pushed the key ON/OFF, whereafter the carriage 6 moves to its predetermined starting position. The light emitting diode under the text SELECT MODE on the display lights up. The operator follows this request and pushes the key FM, which results in that the display "SELECT TUBE SIZE" will light up and the light emitting diode SELECT MODE is turned off and the light emitting diode FM is turned on. The operator follows the request and selects test glass size 2 by pushing the numerical key 2, whereafter he pushes the key ENTER STEP. In this case the displays "TUBE SIZE 2" and "SELECT TIME" will light up. The operator follows the request and pushes the numerical keys ③ ⊡ and ⑤ whereafter he pushes the key ENTER STEP. On the display unit the displays "TUBE SIZE 2", "TIME 3.5" and the display "SELECT LAST FRACTION" will now shine. The operator follows the last request and accordingly feeds in the number 65, whereafter he pushes the key ENTER STEP. This will mean that the displays "TUBE SIZE 2", "TIME 3.5", "LAST FRACTION 65" will be turned on on the presentation unit. Thereby the programming is finished and the fractionation will start when the operator pushes the key RUN.

The programming process mentioned above is illustrated on page 23, where the heads of the table represent the displays and light emitting diodes of the presentation unit. The letter S is an abbreviation for SELECT, T is an abbreviation of TIME, V is an abbreviation of VOLUME, TS is an abbreviation of TUBE SIZE, and LF an abbreviation of LAST FRACTION. Each 0 in the table head is a 7-segment figure that can represent any of the figures 0, 1, . . . , 9. An X under one of the table heads means that the corresponding display/light emitting diode lights up, while a figure under one of the zeros means that the corresponding figure is shown by the 7-segment figure. As can be seen from page 23 the display TIME will count the time backwards from 3.5 minutes in intervals of 0.1 minutes (= 6 s.) The display LAST FRACTION continuously shows the number of test glasses that are to be filled, in this case 65. When the test glass has been filled all the displays with the exception of LAST FRACTION are turned off.

EXAMPLE 2

RACK MODE. One wishes to perform a fractionation with mixed tube sizes and transitions between time base and volume base according to the following schedule:

| Holder No. | Tube size (TS) | Number of tubes/holder | Time/Volume |
|---|---|---|---|
| 1 | 3 | 2 | 87.6 min. |
| 2 | 2 | 6 | 130 drops |
| 3 | 1 | full (= 20) | 20 drops |
| 4 | 3 | 1 | 45 min. |

The program loading is performed in accordance with the table on page 24 and is similar to the loading in connection with example 1 with the exception that "LAST FRACTION" has to be specified for each test glass holder. If all of the test glass holders in a holder are to be filled the corresponding figure (as 20 in the example above for tube size 2) does not have to be specified. The facility has been included that the operator only has to push the key ENTER STEP on extra time.

During the automatic execution phase, which is not illustrated on page 24, but which is similar to the corresponding phase for the example 1, the presentation unit continuously shows the number of the test glass holder that is being filled, the number of test glasses in this holder to be filled and the remaining time interval (or the number of drops to be filled in each tube) before the drop discharge device shall move to the next glass. It is thus possible at any time to determine where in the program the drop discharge device is to be found.

During loading of a program there is an automatic check, as has been mentioned above, that incorrect information is not programmed into the apparatus. Such a programming check is that a loaded value for the tube size only can be 1, 2 or 3. Furthermore it is that in connection with selection of tube size 1, 2 and 3, respectively, LAST FRACTION (= the number of tubes to be filled in the group) in a test glass holder must be less than or equal to 30, 20 and 5 respectively. Further programming checks are also included, but they do not constitute a part of the invention and are for this reason not described in detail. The program according to which the programming check is performed are stored in the main memory of the machine.

The functions that can be programmed into the fraction collector by means of the input unit have been described above. Furthermore there have been described two examples of different programs. Before the programming of the fraction collector can start it is, however, necessary that the operator turns on the power supply by pushing the key "ON". When this is done the stepping motors are reset, that is they are returning the carriage to its starting point, that preferably constitutes the origin in the assumed coordinate system mentioned on page 18. Furthermore there is emitted a CLEAR-pulse that resets certain memory units. Thereafter the program loading can begin.

The described embodiment of the present invention can be changed and modified within the scope of the invention.

TABLE 1

| PROGRAM STEP NO. | Key to push | SM-lamp | FM-lamp | RM-lamp | STOP-lamp | RUN-lamp | R 0 0 | S TS 0 | DISPLAY S T V 0 0. 0. | S LF 0 0 0 |
|---|---|---|---|---|---|---|---|---|---|---|
| 1 | ON/OFF | X | | | X | | | X 0 | X 0 0 0 | X 0 0 0 |
| 2 | FM | | X | | X | | X X 0 | X X 0 | X 0 0 0 | X 0 0 0 |
| 3 | 2 | | X | | X | | X X 2 | X 2 | X 0 0 0 | X 0 0 0 |
| 4 | ENTER STEP | | X | | X | | | X 2 | X X 0 0 0 | X 0 0 0 |
| 5 | 3 . 5 | | X | | X | | | X 2 | X X 3. 5 | X 0 0 0 |
| 6 | ENTER STEP | | X | | X | | | X 2 | X 3. 5 | X X 0 0 0 |
| 7 | 6 5 | | X | | X | | | X 2 | X 3. 5 | X X 0 6 5 |
| 8 | ENTER STEP | | X | | X | | | X 2 | X 3. 5 | X 0 6 5 |
| 9 | RUN | | X | | | X | | | | |
| | | | | | | | | X 2 | X 3. 5 | X 0 6 5 |
| | | | | | | | | X 2 | X 3. 4 | X 0 6 5 |
| | | | | | | | | . | . | . |
| | | | | | | | | . | . | . |
| | | | | | | | | X 2 | X 0. 0 | X 0 6 5 |
| | Test glass change → | | | | | | | | | |
| | | | | | | | | X 2 | X 3. 5 | X 0 6 5 |
| | | | | | | | | X 2 | 3. 4 | X 0 6 5 |
| | | | | | | | | . | . | . |
| | | | | | | | X | | | |

TABLE 2

| Holder | TS | Glasses/holder | Time/Volume |
|---|---|---|---|
| 1 | 3 | 2 | 87,6 min. |
| 2 | 2 | 6 | 130 drops |

TABLE 2-continued

| Holder | TS | Glasses/holder | Time/Volume |
|---|---|---|---|
| 3 | 1 | full = 20 | 20 drops |
| 4 | 3 | 1 | 45 min. |

TABLE 3

| PROGRAM STEP NO. | Key to push | SM-lamp | FM-lamp | RM-lamp | STOP-lamp | RUN-lamp | R 0 0 | S TS 0 | DISPLAY S T V 0 0. 0. | S LF 0 0 0 |
|---|---|---|---|---|---|---|---|---|---|---|
| 1 | CLEAR PROGR. | X | | | X | | | X 0 | X 0 0 0 | X 0 0 0 |
| 2 | RACK MODE | | | X | X | | X 0 1 | X X 0 | X 0 0 0 | X 0 0 0 |
| 3 | 3 | | | X | X | | X 0 1 | X X 3 | X 0 0 0 | X 0 0 0 |
| 4 | ENTER STEP | | | X | X | | X 0 1 | X 3 | X X 0 0 0 | X 0 0 0 |
| 5 | 8 7 . 6 | | | X | X | | X 0 1 | X 3 | X X 8 7. 6 | X 0 0 0 |
| 6 | ENTER STEP | | | X | X | | X 0 1 | X 3 | X 8 7. 6 | X X 0 0 0 |
| 7 | 2 | | | X | X | | X 0 1 | X 3 | X 8 7. 6 | X X 0 0 2 |
| 8 | ENTER STEP | | | X | X | | X 0 2 | X 0 | X 0 0 0 | X 0 0 0 |
| 9 | ENTER STEP | | | X | X | | X 0 2 | X X 0 | X 0 0 0 | X 0 0 0 |
| 10 | 2 | | | X | X | | X 0 2 | X X 2 | X 0 0 0 | X 0 0 0 |
| 11 | ENTER STEP | | | X | X | | X 0 2 | X 2 | X X 0 0 0 | X 0 0 0 |

TABLE 3-continued

| PROGRAM STEP NO. | Key to push | SM—lamp FM—lamp RM—lamp STOP—lamp RUN—lamp | DISPLAY R 0 0 | S TS 0 | S T V 0 0. 0. | S LF 0 0 0 |
|---|---|---|---|---|---|---|
| 12 | T/V | X X | X 0 2 | X 2 | X   X 0 0 0 | X 0 0 0 |
| 13 | 1 3 0 | X X | X 0 2 | X 2 | X   X 1 3 0 | X 0 0 0 |
| 14 | ENTER STEP | X X | X 0 2 | X 2 | X 1 3 0 | X X 0 0 0 |
| 15 | 6 | X X | X 0 2 | X 2 | X 1 3 0 | X X 0 0 6 |
| 16 | ENTER STEP | X X | X 0 3 | X 0 | X 0 0 0 | |
| 17 | ENTER STEP | X X | X 0 3 | X X 0 | X 0 0 0 | X 0 0 0 |
| 18 | 1 | X X | X 0 3 | X X 1 | X 0 0 0 | X 0 0 0 |
| 19 | ENTER STEP | X X | X 0 3 | X 1 | X X 0 0 0 | X 0 0 0 |
| 20 | T/V | X X | X 0 3 | X 1 | X   X 0 0 0 | X 0 0 0 |
| 21 | 2 0 | X X | X 0 3 | X 1 | X   X 0 2 0 | X 0 0 0 |
| 22 | ENTER STEP | X X | X 0 3 | X 1 | X 0 2 0 | X X 0 0 0 |
| 23 | ENTER STEP | X X | X 0 4 | X 0 | X 0 0 0 | X 0 0 0 |
| 24 | ENTER STEP | X X | X 0 4 | X X 0 | X 0 0 0 | X 0 0 0 |
| 25 | 3 | X X | X 0 4 | X X 3 | X 0 0 0 | X 0 0 0 |
| 26 | ENTER STEP | X X | X 0 4 | X 3 | X X 0 0 0 | X 0 0 0 |
| 27 | 4 5 | X  X | X 0 4 | X 3 | X X 0 4 5 | X 0 0 0 |
| 28 | ENTER STEP | X X | X 0 4 | X 3 | X 0 4 5 | X X 0 0 0 |
| 29 | 1 | X X | X 0 4 | X 3 | X 0 4 5 | X X 0 0 1 |
| 30 | ENTER STEP | X X | X 0 5 | X 0 | X 0 0 0 | X 0 0 0 |
| 31 | RUN | X   X | | | | |

What we claim is:

1. A method of controlling the movement of a drop discharge device for dispensing fluid in a fraction collector wherein the drop discharge device is moved across plural test containers disposed in an array of two or more rows, the center to center distances between adjacent test containers in a row being the same, the center to center distances between adjacent test containers in at least one of said rows being different from the center to center distances between adjacent test containers in at least another of said rows, comprising:

storing in a memory information representative of plural preselected basic patterns of coordinate positions corresponding to the locations of each of said test containers in said array, storing in said memory for each basic pattern of coordinate positions plural preselected sub-patterns of coordinate positions corresponding to the locations of test containers at which fluid is to be introduced into a container by said drop discharge device, selecting one or more of said stored basic patterns of coordinate positions and at least one of said sub-patterns of coordinate positions associated therewith, storing in a memory information representative of the number of drops of fluid to be dispensed by said drop discharge device at each of said coordinate positions in said selected subpatterns, automatically moving the drop discharge device in discrete steps across and between said rows of test containers, counting the number of discrete steps of movement of the drop discharge device across and between said rows, stopping the drop discharge device when the counted number of discrete steps corresponds to a coordinate position in a sub-pattern selected from memory.

causing said drop discharge device to dispense fluid while said device is stopped, and automatically resuming movement of the drop discharge device in discrete steps when said predetermined number of drops indicated by said stored information has been counted.

2. A method of controlling the movement of a drop discharge device for dispensing fluid in a fraction collector wherein the drop discharge device is moved across plural test containers disposed in an array of two or more rows, the center to center distances between adjacent test containers is a row being the same, the center to center distances between adjacent test containers in at least one of said rows being different from the center to center distances between adjacent test containers in at least another of said rows, comprising:
- storing in a memory information representative of plural preselected basic patterns of coordinate positions corresponding to the locations of each of said test containers in said array,
- storing in said memory for each basic pattern of coordinate positions plural preselected sub-patterns of coordinate positions corresponding to the locations of test containers at which fluid is to be introduced into a container by said drop discharge device,
- selecting one or more of said stored basic patterns of coordinate positions and at least one of said sub-patterns of coordinate positions associated therewith,
- storing in a memory information representative of the interval of time during which said drop discharge device is to be stopped at each of said coordinate positions in said selected sub-patterns,
- automatically moving the drop discharge device in discrete steps across and between said rows of test containers,
- counting the number of discrete steps of movement of the drop discharge device across and between said rows,
- stopping the drop discharge device when the counted number of discrete steps corresponds to a coordinate position in a sub-pattern selected from memory,
- causing said drop discharge device to dispense fluid while said device is stopped, nd
- automatically resuming movement of the drop discharge device when said predetermined interval of time indicated by said stored information has expired.

3. The method according to claim 2 wherein the information representative of a coordinate position comprises a pair of first and second integers, said first integer representing the number of steps of movement of the drop discharge device across a row to the test container located at that coordinate position in said row, and the second integer representing the number of steps of movement of the drop discharge device between rows to that coordinate position.

4. The method according to claim 3 wherein said step of automatically moving the drop discharge device includes moving the drop discharge device across said rows of test containers in alternating opposite directions.

5. Apparatus for selectively dispensing fluid into plural test containers arranged in rows, the center to center distances between adjacent test containers in a row being the same but the center to center distances between adjacent test containers in at least one of said rows being different from the center to center distances between adjacent test containers in at least another of said rows, comprising:
- a drop discharge device for dispensing fluid,
- a carriage adapted for reciprocating motion across said rows of test containers,
- an arm adapted for movement transverse to the direction of movement of the carriage,
- said carriage being mounted on said arm,
- said drop discharge device being mounted on said carriage,
- first and second stepping motors for transporting the carriage and the arm respectively in discrete steps across and between said rows of test containers,
- a memory containing information representative of plural preselected basic patterns of coordinate positions corresponding to the locations of each of said test containers,
- means for storing in said memory information representative of plural preselected sub-patterns of coordinate positions corresponding to the locations of test containers at which fluid is to be introduced into a container by said drop discharge device,
- means for selecting one or more of said stored basic patterns of coordinate positions from said memory and at least one of said sub-patterns of coordinate positions associated therewith,
- means for storing in said memory information representative of the number of drops of fluid to be dispensed by said drop discharge device at each of said coordinate positions in said selected sub-patterns, and
- control means for causing said first and second stepping motors to move said carriage and said arm such that said drop discharge device moves in discrete steps across and between said rows of test containers in accordance with said selected sub-patterns of coordinate positions and said stored information representative of the number of drops of fluid to be dispensed by said drop discharge device at each of said coordinate positions in said selected sub-patterns.

6. Apparatus for selectively dispensing fluid into plural test containers arranged in rows, the center to center distances between adjacent test containers in a row being the same but the center to center distances between adjacent test containers in at least one of said rows being different from the center to center distances between adjacent test containers in at least another of said rows, comprising:
- a drop discharge device for dispensing fluid,
- a carriage adapted for reciprocating motion across said rows of test containers,
- an arm adapted for movement transverse to the direction of movement of the carriage,
- said carriage being mounted on said arm,
- said drop discharge device being mounted on said carriage,
- first and second stepping motors for transporting the carriage and the arm respectively in discrete steps across and between said rows of test containers,
- a memory containing information representative of plural preselected basic patterns of coordinate positions corresponding to the locations of each of said test containers and,
- means for storing in said memory information representative of plural preselected sub-patterns of coordinate positions corresponding to the locations of test containers at which fluid is to be introduced into a container by said drop discharge device,
- means for selecting one or more of said stored basic patterns of coordinate positions from said memory and at least one of said sub-patterns of coordinate positions associated therewith,
- means for storing in said memory information representative of the intervals of time during which the drop discharge device is to be stopped at each of said coordinate positions in said selected sub-patterns, and
- control means for causing said first and second stepping motors to move said carriage and said arm such that said drop discharge device moves in discrete steps across and between said rows of test containers in accordance with said selected sub-patterns of coordinate positions and said stored information representative of the number of drops of fluid to be dispensed by said drop discharge device at each of said coordinate positions in said selected sub-patterns.

7. Apparatus to claim 6 wherein said control means includes first and second counters for counting the number of discrete steps of movement of said drop discharge device across and between said rows of test containers respectively, comparator means for comparing the counts of said first and second counters to said coordinate positions of said sub-patterns selected from memory, and means connected to said comparator means for temporarily stopping said stepping motors when the counts of said counters match a coordinate position in said selected sub-patterns.

8. Apparatus according to claim 7 wherein said means for temporarily stopping said stepping motors includes a drop counter for counting the number of drops of fluid dispensed by said drop discharge device.

9. Apparatus according to claim 7 wherein said means for temporarily stopping said stepping motors includes a time counter for counting the time during which the drop discharge device is stopped at a preselected coordinate position.

10. Apparatus according to claim 7 wherein said means for temporarily stopping said stepping motors includes means for causing said drop discharge device to descend towards a test container when said drop discharge device is stopped at a coordinate position at which the test container is located, and means for preventing said drop discharge device from descending towards a test container unless said drop discharge device has stopped at the coordinate position at which the test container is located.

11. The method according to claim 1 wherein the information representative of a coordinate position comprises a pair of first and second integers, said first integer representing the number of steps of movement of the drop discharge device across a row to the test container located at that coordinate position in said row, and the second integer representing the number of steps of movement of the drop discharge device between rows to that coordinate position.

12. The method according to claim 11 wherein said step of automatically moving the drop discharge device includes moving the drop discharge device across said rows of test containers in alternate opposite directions.

13. Apparatus according to claim 5 wherein said control means includes first and second counters for counting the number of discrete steps of movement of said drop discharge device across and between said rows of test containers respectively, comparator means for comparing the counts of said first and said second counters to said coordinate positions of said sub-patterns selected from memory, and means connected to said comparator means for temporarily stopping said stepping motors when the counts of said counters match a coordinate position in said selected sub-patterns.

14. Apparatus according to claim 13 wherein said means for temporarily stopping said stepping motors includes a drop counter for counting the number of drops of fluid dispensed by said drop discharge device.

15. Apparatus according to claim 13 wherein said means for temporarily stopping said stepping motors includes a time counter for counting the time during which the drop discharge device is stopped at a preselected coordinate position.

16. Apparatus according to claim 13 wherein said means for temporarily stopping said stepping motors includes means for causing said drop discharge device to descend towards a test container when said drop discharge device is stopped at a coordinate position at which the test container is located, and means for preventing said drop discharge device from descending towards a test container unless said drop discharge device has stopped at the coordinate position at which the test container is located.

* * * * *